(12) United States Patent
Wade et al.

(10) Patent No.: US 9,289,332 B2
(45) Date of Patent: Mar. 22, 2016

(54) DISPOSABLE ABSORBENT PANTS WITH ADVANTAGEOUS STRETCH AND MANUFACTURABILITY FEATURES, AND METHODS FOR MANUFACTURING THE SAME

(71) Applicant: The Procter & Gamble Company, Cincinnati, OH (US)

(72) Inventors: Sarah Marie Wade, Springfield Township, OH (US); Gary Dean Lavon, Liberty Township, OH (US); Miguel Alvaro Robles, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 140 days.

(21) Appl. No.: 13/893,604

(22) Filed: May 14, 2013

(65) Prior Publication Data
US 2013/0310793 A1 Nov. 21, 2013

Related U.S. Application Data

(60) Provisional application No. 61/646,923, filed on May 15, 2012.

(51) Int. Cl.
*A61F 13/15* (2006.01)
*A61F 13/49* (2006.01)

(52) U.S. Cl.
CPC ....... *A61F 13/49019* (2013.01); *A61F 13/4902* (2013.01); *A61F 13/49011* (2013.01); *A61F 13/49017* (2013.01)

(58) Field of Classification Search
CPC .................... A61F 13/49011; A61F 13/49017;
A61F 13/49019; A61F 13/4902; A61F 13/49012; A61F 13/4906; A61F 13/49061; A61F 13/49058
See application file for complete search history.

(56) References Cited

U.S. PATENT DOCUMENTS

| | | | |
|---|---|---|---|
| 3,848,594 A | 11/1974 | Buell | |
| 4,662,875 A | 5/1987 | Hirotsu et al. | |
| 4,699,622 A | 10/1987 | Toussant et al. | |
| 4,846,815 A | 7/1989 | Scripps | |
| 4,894,060 A | 1/1990 | Nestegard | |
| 4,946,527 A | 8/1990 | Battrell | |
| 5,143,679 A | 9/1992 | Weber et al. | |
| 5,151,092 A | 9/1992 | Buell et al. | |
| 5,156,793 A | 10/1992 | Buell et al. | |
| 5,167,897 A | 12/1992 | Weber et al. | |
| 5,221,274 A | 6/1993 | Buell et al. | |
| 6,428,526 B1 | 8/2002 | Heindel et al. | |
| 6,432,098 B1 | 8/2002 | Kline et al. | |
| 6,447,497 B1 | 9/2002 | Olson | |
| 6,626,879 B1 | 9/2003 | Ashton et al. | |
| 6,923,797 B2 * | 8/2005 | Shinohara et al. | 604/385.27 |
| 6,991,622 B2 * | 1/2006 | Nakaoka et al. | 604/385.201 |
| 7,056,411 B2 | 6/2006 | Desai et al. | |
| 7,833,211 B2 | 11/2010 | Mansfield et al. | |
| 8,062,454 B2 | 11/2011 | Yamamoto et al. | |

(Continued)

OTHER PUBLICATIONS http://dictionary.reference.com/browse/transversely, May 12, 2015.*

(Continued)

*Primary Examiner* — Bradley Philips
(74) *Attorney, Agent, or Firm* — Andrew J. Mueller

(57) ABSTRACT

A disposable absorbent pant that includes a central chassis and a belt structure is disclosed herein.

10 Claims, 23 Drawing Sheets

(56) References Cited

U.S. PATENT DOCUMENTS

| | | |
|---|---|---|
| 8,075,722 B2 | 12/2011 | Takahashi et al. |
| 8,171,972 B2 | 5/2012 | Eckstein et al. |
| 8,177,766 B2 | 5/2012 | Mansfield |
| 8,182,627 B2 | 5/2012 | Eckstein et al. |
| 8,193,407 B2 | 6/2012 | Mansfield et al. |
| 8,372,053 B2 | 2/2013 | Shimada et al. |
| 8,986,276 B2 | 3/2015 | Kawakami et al. |
| 2003/0091807 A1 | 5/2003 | Desai et al. |
| 2004/0222553 A1 | 11/2004 | Desai et al. |
| 2005/0004549 A1* | 1/2005 | Maas et al. ............. 604/385.29 |
| 2005/0222546 A1 | 10/2005 | Vargo et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0275909 A1* | 11/2009 | Sakaguchi ............. 604/385.23 |
| 2010/0193135 A1 | 8/2010 | Eckstein et al. |
| 2012/0022485 A1 | 1/2012 | Roe et al. |
| 2012/0157955 A1 | 6/2012 | Ashton et al. |
| 2012/0193138 A1 | 8/2012 | Jones |
| 2012/0271265 A1 | 10/2012 | Langdon |

OTHER PUBLICATIONS

U.S. Appl. No. 13/447,585, filed Apr. 16, 2012, Papsdorf.
U.S. Appl. No. 13/457,521, filed Apr. 27, 2012, Goodlander.

* cited by examiner

DISPOSABLE ABSORBENT PANTS WITH ADVANTAGEOUS STRETCH AND MANUFACTURABILITY FEATURES, AND METHODS FOR MANUFACTURING THE SAME

BACKGROUND

Currently, disposable absorbent pants are manufactured and marketed for wear by toddlers and young children who are not yet toilet trained, older children who are experiencing childhood enuresis, and adults suffering from incontinence. A disposable absorbent pant usually includes a central chassis having a core formed of absorbent material, enveloped between a liquid permeable, wearer-facing topsheet, and a liquid impermeable, outer- or garment-facing backsheet. The chassis is usually adapted to be positioned on the wearer such that it wraps between the wearer's legs and upwardly about the lower torso, such that the front and rear ends extend toward the wearer's waistline in the front and rear, respectively. The chassis is often joined to a pair of side/hip panels that connect front and rear regions of the chassis on either side thereof, thereby forming a pant structure. In many current designs, the side/hip panels are manufactured so as to be elastically extensible in the lateral direction, providing stretchability that eases donning, while providing a relatively snug and comfortable fit once donned. Disposable absorbent pants are usually manufactured in one of two differing overall configurations.

In the first configuration, the backsheet and topsheet of the central chassis structure extend to, and form, the front and rear waist edges of the pant in the regions near the wearer's navel in the front, and small of the back in the rear. Separate and discrete side/hip panels are joined to longitudinal (side) edges of the central chassis structure in its front and rear regions, joining them to form the pant structure. An example of this type of configuration is currently manufactured and sold in the United States by The Procter & Gamble Company under the trademark PAMPERS EASY UPS.

In the second configuration, the central chassis structure does not extend to, or form, the front and rear waist edges of the pant. Rather, an elasticized belt structure entirely encircles the wearer's waist and forms the waist edge about the entire pant, and the side/hip panels. The central chassis is joined to the belt structure, usually on the inside thereof, with its ends disposed at locations in the front and rear waist regions somewhat below the waist edges of the belt structure. This second configuration is sometimes known as a "belt" or "balloon" configuration (hereinafter, "belt" configuration). An example of this type of configuration is currently manufactured and sold in Asia by The Procter & Gamble Company under the trademark PAMPERS, and also by Unicharm Corporation under the trademark MAMY POKO.

While both configurations have their advantages, in some circumstances a belt configuration may be deemed desirable. Among other advantages, because the encircling belt may be made elastically extensible in the lateral direction, considerable elastic stretch and contraction as well as targeted elastic profiles may be provided entirely about the wearer's waist.

For purposes of optimal fit, appearance and containment, it may be desired that a pant have elastic extensibility not only laterally hoop-wise about the waist and hips, but also hoop-wise about each of the legs, so as to provide an elasticized leg band or leg band-like structure. This may be accomplished by incorporating elastic members into the structure that at least partially encircle the leg openings, in addition to the laterally extending elastic members encircling the waist opening.

Although some currently manufactured belt configuration pants include such an arrangement of elastic members, they could be deemed to have a rough or unfinished appearance, or are inefficient to manufacture, or both. For example, some current designs have elastic members that continue across front and rear regions of the chassis, having no important function and creating an unsightly appearance.

Therefore, improvements to the design of disposable absorbent pants of a belt configuration, that provide for elasticized leg band-like features that and also efficient manufacturability, would be advantageous.

DESCRIPTION OF EXAMPLES

Definitions

"Cross direction" (CD)—with respect to the making of a nonwoven web material, the nonwoven material itself, a laminate thereof, or an article in which the material is a component, refers to the direction along the material substantially perpendicular to the direction of forward travel of the material through the manufacturing line in which the material and/or article is manufactured.

As used herein, the term "elastic" or "elastomeric" refers to the property of an extensible material (or a composite of multiple materials) that can extend, without substantial rupture or breakage, to a strain of 100% in the Hysteresis Test, with a set less than or equal to 10% of the elongation as measured according to the Hysteresis Test. An elastic material is considered elastically extensible.

"Machine direction" (MD)—with respect to the making of a nonwoven web material, the nonwoven material itself, a laminate thereof, or an article in which the material is a component, refers to the direction along the material substantially parallel to the direction of forward travel of the material through the manufacturing line in which the material and/or article is manufactured.

"Lateral"—with respect to a pant and its wearer, refers to the direction generally perpendicular with the wearer's standing height, or the horizontal direction when the wearer is standing. "Lateral" is also the direction generally perpendicular to a line extending from the midpoint of the front waist edge to the midpoint of the rear waist edge.

"Longitudinal"—with respect to a pant and its wearer, refers to the direction generally parallel with the wearer's standing height, or the vertical direction when the wearer is standing. "Longitudinal" is also the direction generally parallel to a line extending from the midpoint of the front waist edge to the midpoint of the rear waist edge.

Figure 1:
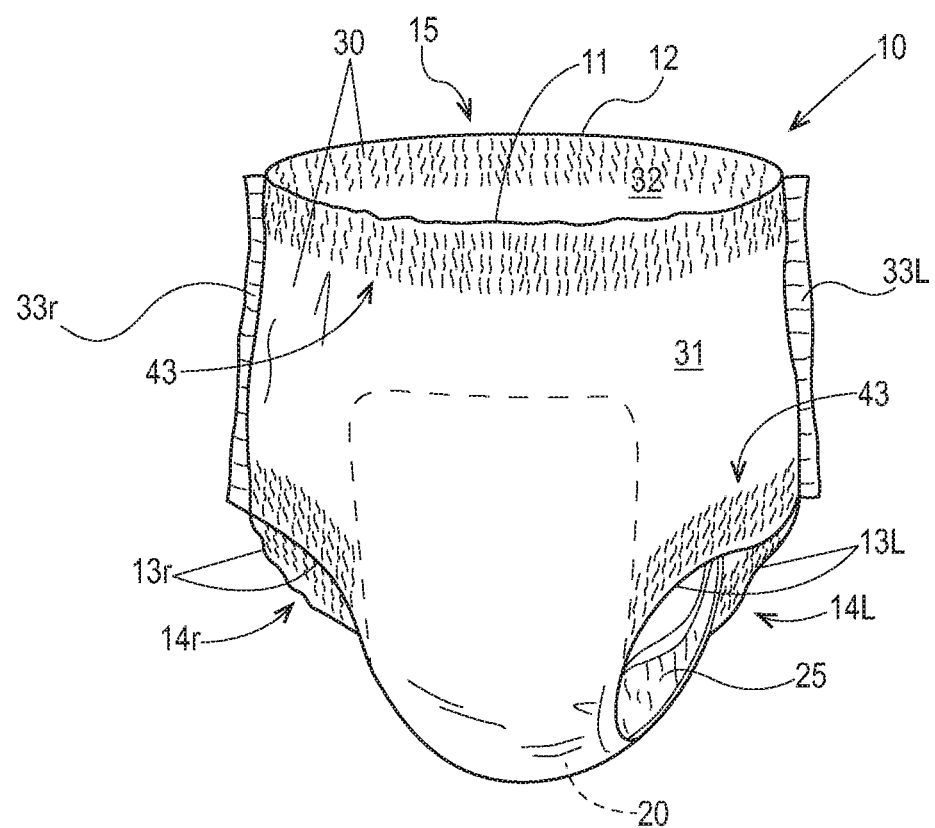
FIG. 1 is simplified perspective view of a disposable absorbent pant.

FIG. 1 is a general simplified perspective depiction of a disposable absorbent pant 10 having a belt configuration. Pant 10 may include a central chassis 20 and a belt structure 30. Belt structure 30 may be elastically extensible in the lateral direction, providing elastic stretchability for ease of donning, and a snug and comfortable fit following donning. Central chassis 20 may include a wearer-facing, liquid permeable topsheet (not specifically shown in FIG. 1), an outer- or garment-facing backsheet (not specifically shown in FIG. 1) and an absorbent core (not specifically shown in FIG. 1) sandwiched or enveloped between the topsheet and backsheet. A pair of laterally opposing, longitudinally extending barrier cuffs 25 also may be included with the central chassis in a crotch region thereof, disposed adjacent to the topsheet. Generally the central chassis and barrier cuffs may have any construction and components, including leg cuff structures, suitable for disposable diapers, training pants, and adult incontinence pants, such as, but not limited to, those described in U.S. provisional patent application No. 61/480,663 and application(s) claiming priority thereto. Belt structure 30 may have a front portion 31 and a rear portion 32. Front and rear portions 31, 32 may be joined together at respective left and right side seams 33*l*, 33*r*. Belt structure 30 may form front and rear waist edges 11, 12 defining waist opening 15, and at least portions of left and right leg opening edges 13*l*, 13*r* of the pant 10.

Figure 2:
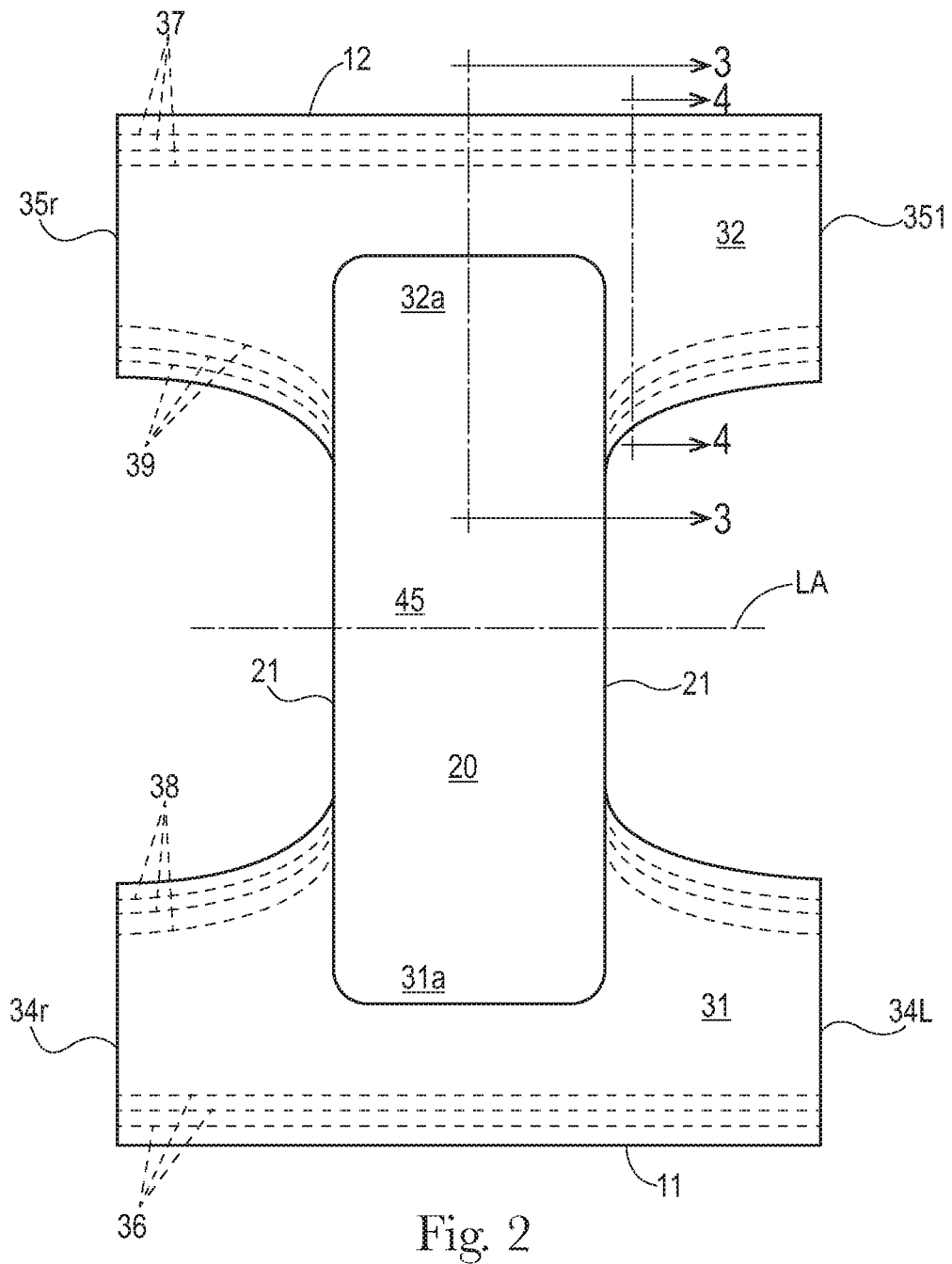
FIG. 2 is a simplified plan view of a precursor structure of a disposable absorbent pant, shown with inner or wearer-facing surfaces upward.

FIG. 2 is a simplified plan view of the precursor structure of the pant 10 shown in FIG. 1, shown prior to joining of front and rear portions 31, 32 along their respective side edges 34*l*, 35*l* and 34*r*, 35*r*. Front region 31*a*, including front portion 31, and rear region 32*a*, including rear portion 32, may each include anywhere from 25 percent to 40 percent of the overall longitudinal length of the precursor structure; correspondingly, a crotch region 45 may include anywhere from 20 percent to 50 percent of the overall longitudinal length of the precursor structure, with at least a portion thereof lying at lateral axis LA. To form pant 10, the precursor structure may be folded along lateral axis LA to bring front and rear regions 31*a*, 32*a*, and front and rear portions 31, 32 together such that their side edges 34*l*, 35*l* and 34*r*, 35*r*, respectively, may be joined at seams 33*l*, 33*r* (as shown in FIG. 1). Seams 33*l*, 33R may be formed by adhesive, thermal, pressure, or ultrasonic bonding, and combinations thereof. In an alternative example, the seams may be formed by mechanical fasteners such as cooperating pairs of hook-and-loop fastening components disposed along side edges 34*r*, 35*r* and 34*l*, 35*l*. Fasteners may also include tape tabs, interlocking fasteners such as tabs & slots, buckles, buttons, snaps, and/or hermaphroditic fastening components. Exemplary surface fastening systems are disclosed in U.S. Pat. Nos. 3,848,594; 4,662,875; 4,846,815; 4,894,060; 4,946,527; 5,151,092; and 5,221,274, while an exemplary interlocking fastening system is disclosed in U.S. Pat. No. 6,432,098. The fastening system may also include primary and secondary fastening systems, as disclosed in U.S. Pat. No. 4,699,622. Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526.

Still referring to FIG. 2, one or both of front and rear portions 31, 32 may include at least a first elastic member 36, 37 disposed nearer the waist edges 11, 12 and at least a second elastic member 38, 39, disposed nearer the leg opening edges 13*l*, 13*r*. As suggested in FIG. 2, one or a plurality of waist elastic members 36, 37 may be disposed in a substantially straight lateral orientation, and one or a plurality of leg elastic members 38, 39 may be disposed along curvilinear paths to provide hoopwise elastic stretch about the leg openings 13*l*, 13*r* (as shown FIG. 1). For purposes of manufacturing a pant having a neat appearance as will be described below, it may be desired that leg elastic members 38, 39 terminate proximate the respective longitudinal edges 21 of chassis 20. For purposes herein, where used to describe a positional relationship between two features, "proximate" is intended to mean within 2.0 cm, more preferably within 1.0 cm, of the identified features.

Elastic members 36, 37, 38 and 39 may be in the form of film or sections or strips thereof, strips, ribbons, bands or strands of circular or any other cross-section, formed in any configuration of any elastomeric material such as described in, for example, co-pending U.S. application Ser. Nos. 11/478,386 and 13/331,695, and U.S. Pat. No. 6,626,879. A suitable example is LYCRA HYFIT strands, a product of Invista, Wichita, Kans.

Figure 3A:
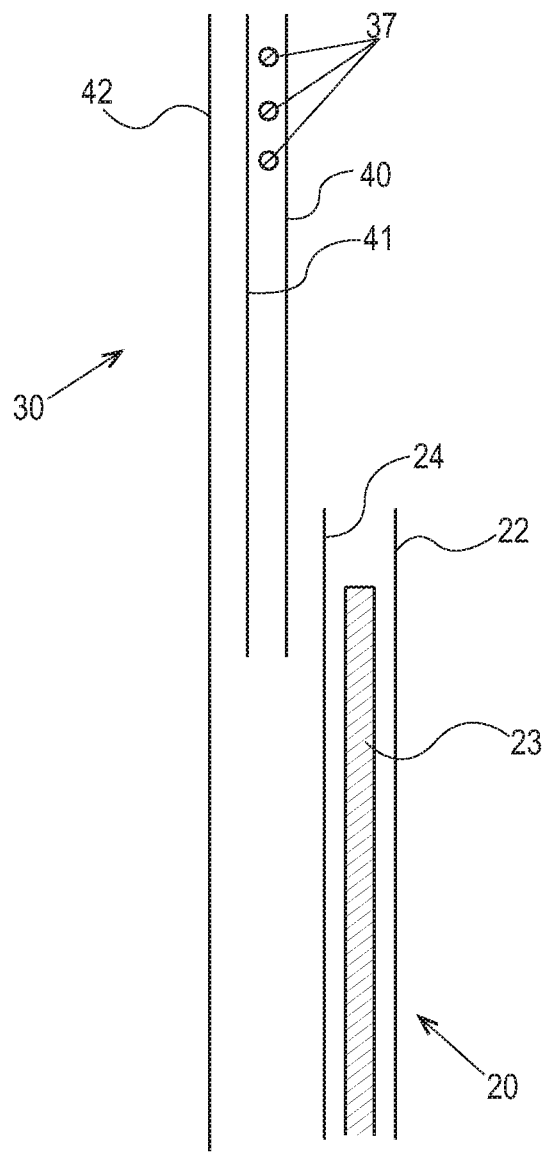
FIG. 3A is a simplified, schematic cross-section view taken through line 3-3 of FIG. 2, in one example of a possible configuration.
Figure 3B:
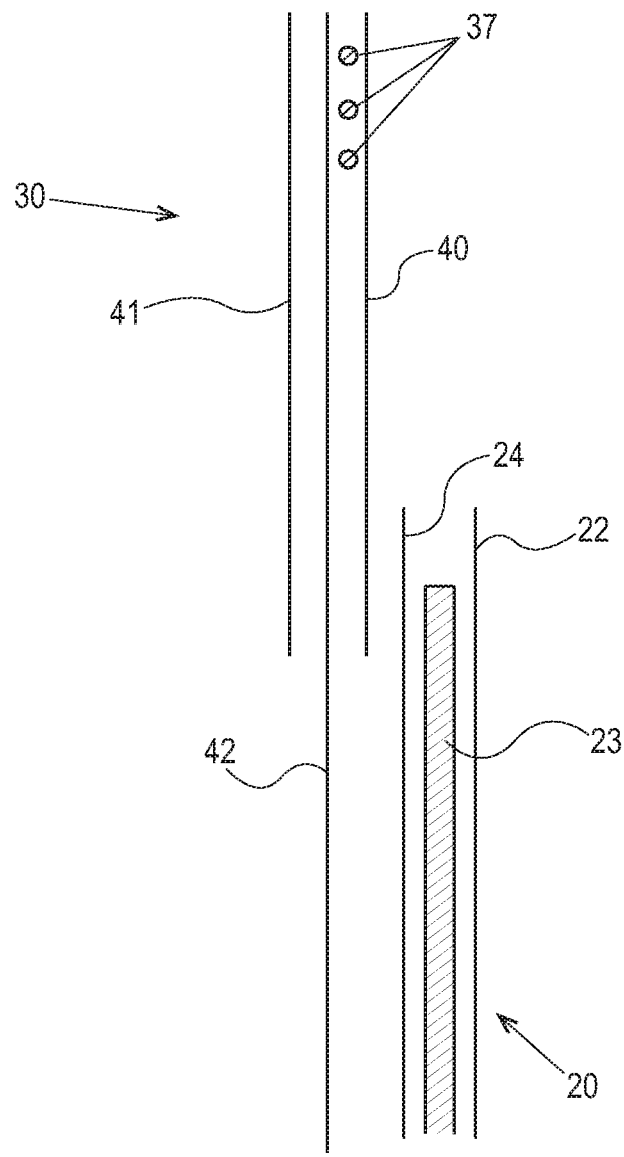
FIG. 3B is a simplified, schematic cross-section view taken through line 3-3 of FIG. 2, in another example of a possible configuration.
Figure 3C:
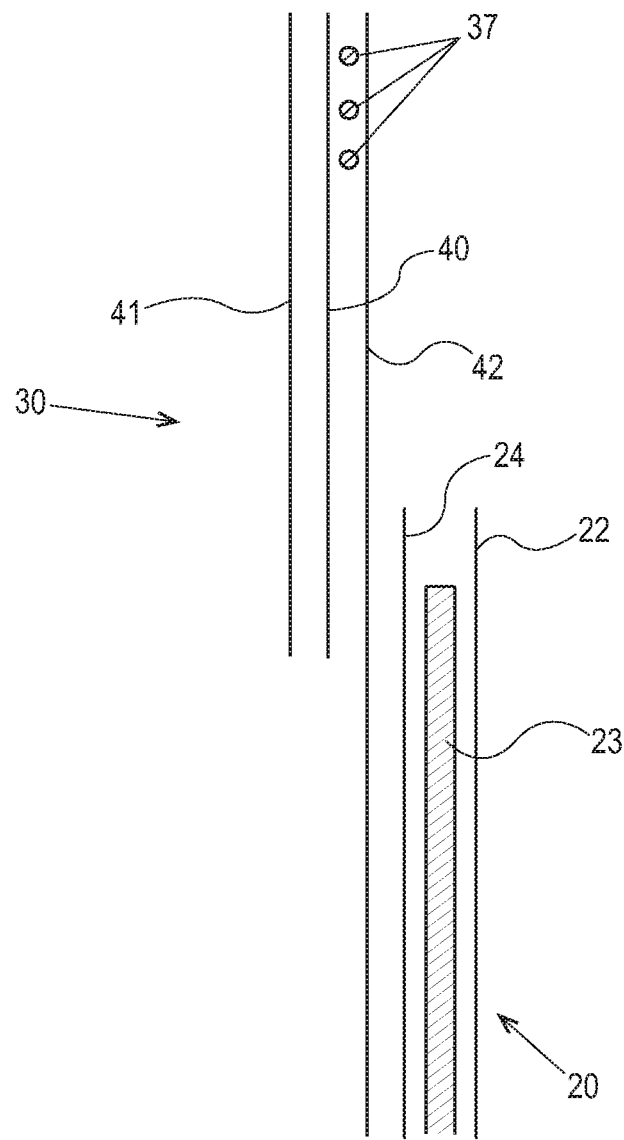
FIG. 3C is a simplified, schematic cross-section view taken through line 3-3 of FIG. 2, in another example of a possible configuration.

FIGS. 3A-3C are examples of potential longitudinal cross-sections taken at line 3-3 through the rear portion 32 of the belt structure and rear region of the pant as shown in FIG. 2, depicting features in three possible configurations. It can be appreciated that in each of these particular examples, the cross-section may substantially mirror a cross-section taken through the front portion 31 of the belt structure and the front region of the pant.

Figure 4A:
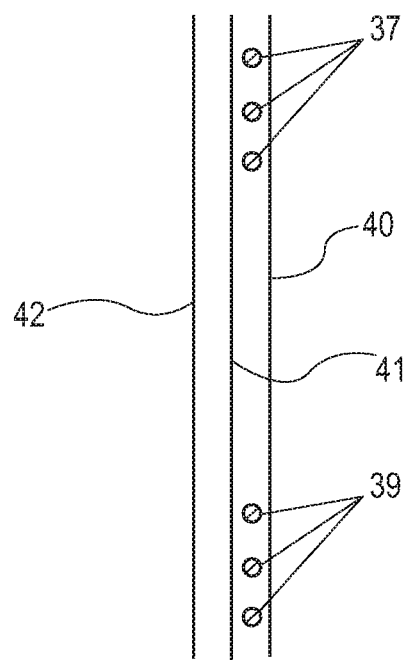
FIGS. 4A-4K are simplified, schematic cross-section views taken through line 4-4 of FIG. 2, in various examples of possible configurations.
Figure 4B:
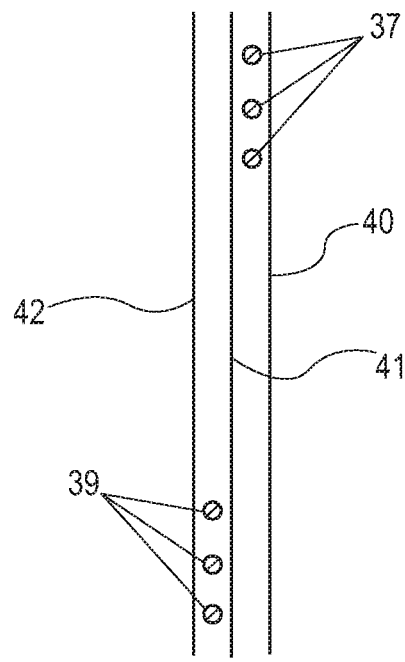
Figure 4C:
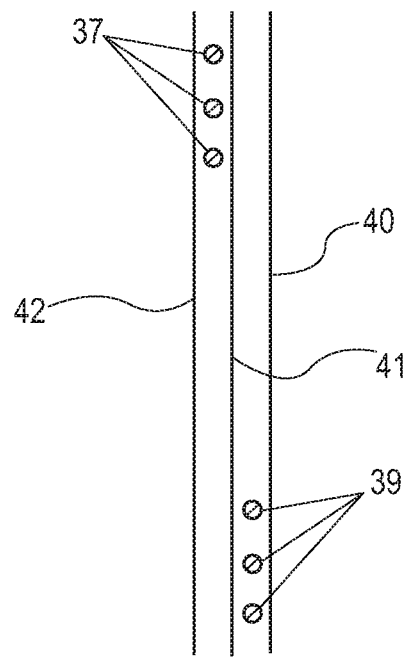
Figure 4D:
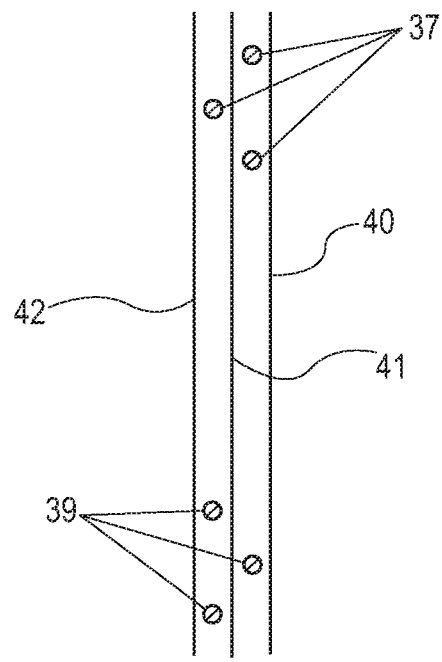
Figure 4E:
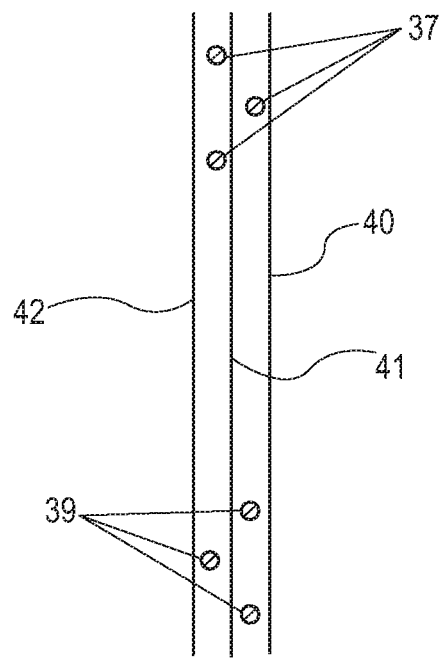

FIG. 4A is an example of a potential longitudinal cross-section taken at line 4-4 through the rear portion 32 of the belt structure and rear region of the pant as shown in FIG. 2, depicting features in one configuration. It can be appreciated that this cross-section may also be a substantial mirror image of a cross-section taken through the front portion 31 of the belt structure and the front region of the pant. Belt structure 30 where shown in FIG. 4A has the same layers and components as those depicted in FIG. 3A, hut with the addition of leg elastic members 39 and without the chassis components, as a result of the location of the cross-section. As suggested in FIG. 2, leg elastic members 39 may terminate proximate the longitudinal edges 21 of central chassis 20; thus, they do not appear in FIGS. 3A and 3B. Additional elastics (not shown) may be disposed longitudinally between the waist elastics and the leg elastics shown in FIGS. 4A-4K.

Referring to FIGS. 3A-3C, chassis 20 may have liquid permeable topsheet 22 forming at least a portion of its inner, wearer-facing surface. Topsheet 22 may be formed of a nonwoven web material which is preferably soft and compatible with sensitive skin, and may be formed of and have any of the features of topsheets used in disposable diapers, training pants and inserts including those described in, for example, co-pending U.S. application Ser. No. 12/841,553. Chassis 20 may also have an outward-facing backsheet 24, which may be liquid impermeable. Backsheet 24 may be formed of and have any of the features of backsheets used in disposable diapers and training pants including those described in, for example, the co-pending U.S. patent application referenced immediately above. Chassis 20 may also have an absorbent core 23 disposed between topsheet 22 and backsheet 24. Absorbent core 23 may include one or more absorbent acquisition, distribution and storage material layers and/or components; it may be formed of and have any of the features of absorbent cores used in disposable diapers and training pants including those described in, for example, the co-pending U.S. patent application referenced immediately above.

As suggested in FIGS. 3A-3C, chassis 20 may be affixed to a belt structure 30, to the inner, wearer-facing side thereof, or alternatively, to the outer, garment-facing surface thereof. Chassis 20 may be bonded to the belt structure 30 by adhesive, by thermal bonds/welds, mechanical fasteners or a combination thereof.

Referring to FIGS. 3A and 4A, belt structure 30 may have a first belt layer 40, which may be formed of a suitable nonwoven web material. Since the first belt layer may come into direct contact with the wearer's skin, it may be deemed preferable to select a nonwoven web material for the layer that is soft, comfortable and relatively breathable/vapor permeable. One or more waist elastic members 37 may be disposed between first belt layer 40 and a second belt layer 41. Second belt layer 41 may be formed of the same, similar or differing nonwoven web material as first belt layer 40. First belt layer 40 and second belt layer 41 may be bonded together by adhesive, a pattern of thermal bonds or a combination thereof such that first belt layer 40 and second belt layer 41 form a laminate, with the one or more waist elastic members 37 sandwiched and affixed there between. Similarly, referring to FIG. 4A, the one or more leg elastic members 39 may be affixed and sandwiched between first belt layer 40 and second belt layer 41.

Figure 8:
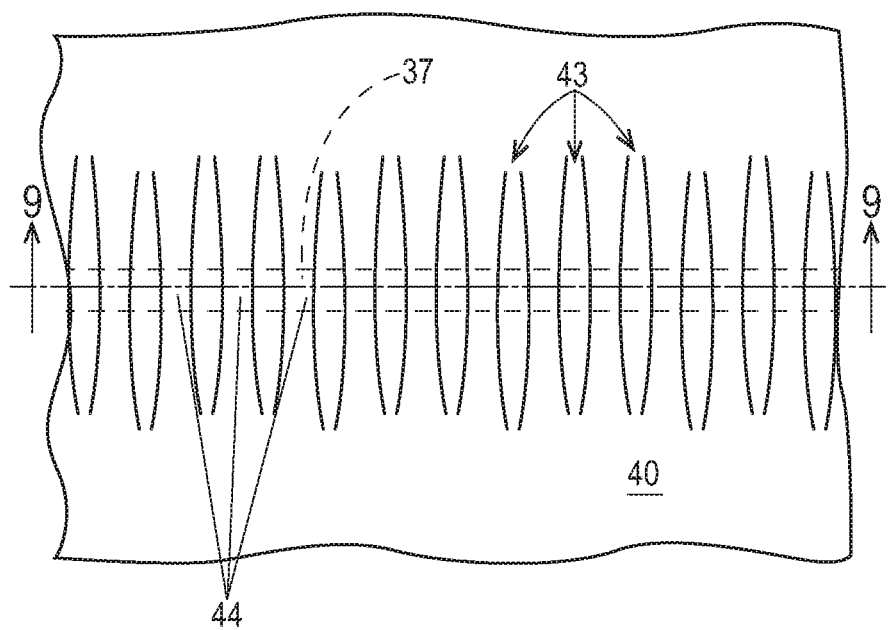
FIG. 8 is a plan view of a portion of a multilayer web including two nonwoven layers and a pre-strained elastic member, with formations of shirrs along the elastic member in the nonwoven layers.
Figure 9:
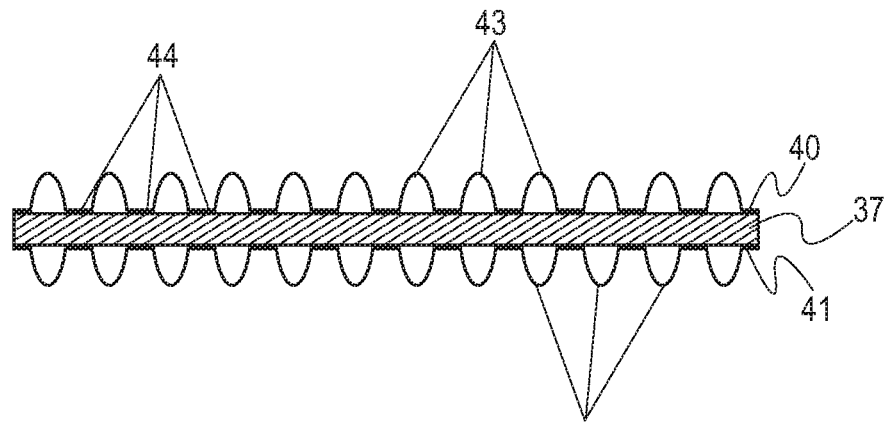
FIG. 9 is a cross-section view along line 9-9 in FIG. 8.

Referring to FIGS. 8 and 9, during manufacture, the one or more waist elastic members 37 may be pre-strained along the direction of their lengths or longer dimensions, before they are affixed between the belt layers, such that, upon completion of manufacture and subsequent relaxation, contraction of elastic members 37 will induce a pattern of wrinkles, pleats, corrugations or rugosities (hereinafter, "shirrs") 43 in first belt layer 40 and second belt layer 41. The shirrs 43 are formed of material that gathers about the elastic members as they contract, and the gathered material serves to accommodate stretching and contraction of the belt structure 30. The shirrs 43 are oriented along fold or bending lines roughly transverse or perpendicular to the direction of lateral contraction of the elastic members 37.

Similarly, the one or more leg elastic members 39 may be pre-strained along their paths of placement (which, as noted, may be curvilinear) during manufacture before they are affixed between the layers, such that, upon completion of manufacture and subsequent relaxation, contraction of elastic members 39 will induce a pattern of shirrs in first belt layer 40 and second belt layer 41. These shirrs are also formed of material that gathers about the elastic members as they contract, and serve to accommodate stretching and contraction of the belt structure 30 about the leg openings. The shirrs are oriented along fold or wrinkle lines roughly transverse or perpendicular to the direction of contraction of the elastic members 39.

Still referring to FIGS. 8 and 9, patterns of deposits of adhesive may be applied to either of the layers 40, 41, and/or to the elastic members 37, 39 to adhere the layers to the elastic members 37, 39 at adhered portions 44, in regular patterns and/or intervals, so that the shirrs formed upon relaxation and contraction of elastic members 37, 39 are somewhat uniform, evenly distributed and neat in appearance.

Also as shown in FIGS. 3A-3C and 4A-4K, the belt structure may include a longitudinally extending wrapping layer 42. Wrapping layer 42 may form a layer that wraps not only about the front and rear portions of the belt structure, but also extends from the front portion, around and beneath the chassis 20 through the crotch region, and into the rear portion. The wrapping layer 42 may be formed of a single material web disposed as a layer of the rear portion 32 of the belt structure 30, the central chassis 20, and the front portion 31 of the belt structure 30. Wrapping layer 42 may be disposed so as to form an outer layer of the belt structure 30 in the front and rear portions as suggested in FIGS. 3A and 4A-4G, an intermediate layer in the front and rear portions as suggested in FIGS. 3B and 4H, or an inner layer as suggested in FIGS. 3C and 4K. Wrapping layer 42 may be formed of any suitable nonwoven web material having desired properties of softness and mechanical strength.

Figure 10A:
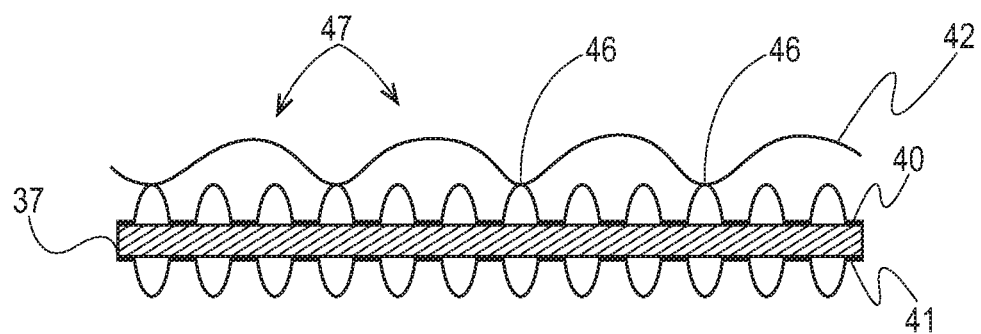
FIGS. 10A-10C are cross-sections similar to that of FIG. 9, but including a third layer and showing examples in which a third layer may be included and attached in an elasticized multilayer web structure and imparted with differing patterns of shirrs.
Figure 10B:
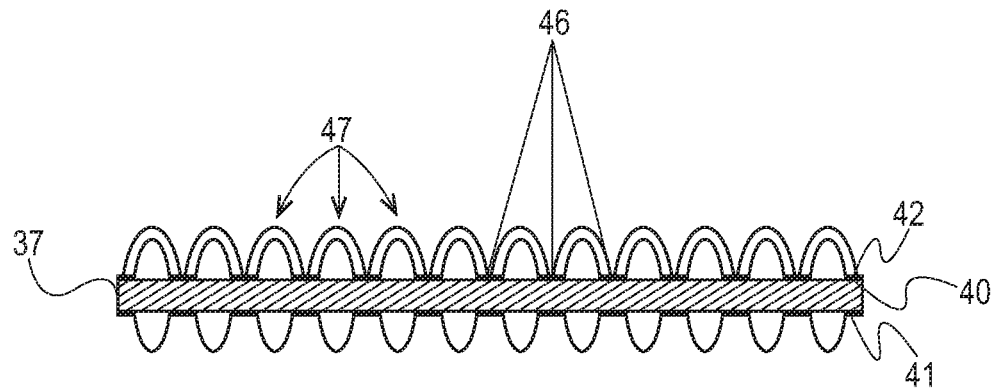
Figure 10C:
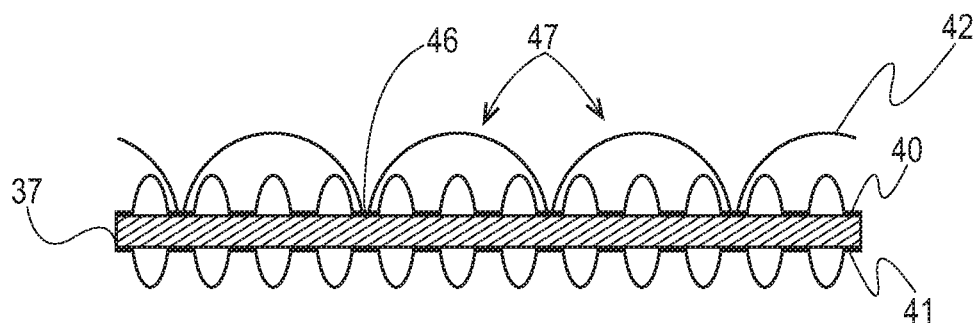

Wrapping layer 42 may be added to the belt structure 30 in a step occurring later than the step in which the first belt layer 40, elastic members 36, 37, 38 and 39, and second belt layer 41 are joined. In some circumstances the shirrs in layers 40, 41 caused by attachment of the elastic members to layers 40 and 41 and relaxation and contraction of elastic members 36, 37, 38 and 39 from a pre-strained state may be formed in a manner to provide a relatively smooth texture and surface against the skin of the wearer. Referring to FIGS. 10A-10C, one advantage provided by a third layer is that, during a step following lamination of the portions of belt structure 30 including layers 40 and 41, with one or more elastic members 36, 37, 38 and 39 there between, the wrapping layer 42 may be joined to the outside surface of second belt layer 41 at attachment points 46 to form a distinct and different configuration of second shirrs 47. As a result, wrapping layer 42 may be imparted with larger second shirrs than exist on first or second belt layers 40, 41, providing an appearance of a greater degree of stretch and/or lofty feel. Differences in appearance and/or height and spacing of shins in the belt laminate formed by, e.g., layers 40, 41 and interposed elastic elements can be achieved by differing the types of adhesive and/or differing patterns of adhesive deposits or mechanical bonds, used to affix wrapping layer 42 to the other layers at attachment points 46. For example, the elastic members may be joined to the first belt layer 40 and second belt layer 41 by a first adhesive or mechanical bond pattern that produces a first configuration of shirrs, and this precursor elasticized multilayer web structure may then be joined to the wrapping layer 42 via a different pattern of adhesive deposits, resulting in a distinctly different configuration of shins from that of the precursor elasticized multilayer web structure. Such a difference may provide for enhanced visual and tactile softness attributes, fewer instances of skin irritation or marking that can result from concentrations of pressure at shirrs, less bulk under clothing, improved stretch and other perceptual advantages. In an alternative example, one or more of the layers 40, 41 and/or 42 may include an extensible porous substrate such as an elastomeric nonwoven material (i.e., a nonwoven material whose fiber constituents are formed of elastomeric polymer(s)) or an elastomeric foam material, which may be applied in a partially strained state, thereby reducing the size of the shirrs in such layer when the belt is in its relaxed, contracted state. Additionally, as may be appreciated from FIG. 3A, in one configuration wrapping layer 42 may be disposed to cover over the junction between central chassis 20 and the belt structure 30, concealing it and further contributing to a smooth, unified outward appearance. It will be appreciated that FIGS. 10A-10C are non limiting examples, and other configurations of three layers of web material with elastic members disposed there between may be manufactured to impart differing patterns of shins in the respective layers.

Examples of suitable nonwoven web materials useful for forming any of layers 40, 41 and 42 are described in co-pending U.S. application Ser. No. 13/090,761.

FIGS. 4B-4K depict alternative configurations that cross-section 4-4 (FIG. 2) may have, according to differing embodiments of a pant with a belt structure having a first belt layer 40, second belt layer 41, and wrapping layer 42. As may be appreciated by a comparison of FIGS. 4A and 4B-4C, and 4D-4E, waist elastic members 36, 37 and leg elastic members 38, 39, may be disposed between differing pairs of layers 40, 41 and 41, 42, and may have alternating dispositions between layers. These varying locations of disposition of elastic members provide for flexibility in manufacturing and/or alteration of the outward appearance of the pant. For example, it may be desired that shirrs imparted by relaxation and contraction of pre-strained elastic members be accentuated at the waist line and/or at the leg band area, which may signal fit and stretchability to the consumer. In this circumstance, it may be desired to dispose, e.g., waist elastic members 36, 37 between an intermediately disposed belt layer and an outwardly-disposed layer. Alternatively, it may be desired that the appearance of shirrs be partially subdued or concealed. In this circumstance, it may be desired to dispose, e.g., leg elastic members 38, 39 between an intermediately-disposed layer and an inwardly-disposed layer. In another alternative, disposing the elastic members between an outwardly-disposed layer and an intermediately-disposed layer may impart a smoother texture to the inwardly-disposed layer, thereby providing a more comfortable surface next to the wearer's skin. In the alternatives depicted in FIGS. 4D and 4E, alternating disposition of elastic members between differing layer pairs may serve to allow a closer longitudinal distribution of elastic members for a greater force profile in one or both of the waist band and leg band areas, than would be achievable if all elastic members are disposed between the same layers, because, during manufacture, it may be difficult to achieve close longitudinal spacing when applying elastic members to a web, without having the members bunch together in some locations—particularly when they are applied along a curvilinear path.

Figure 4F:
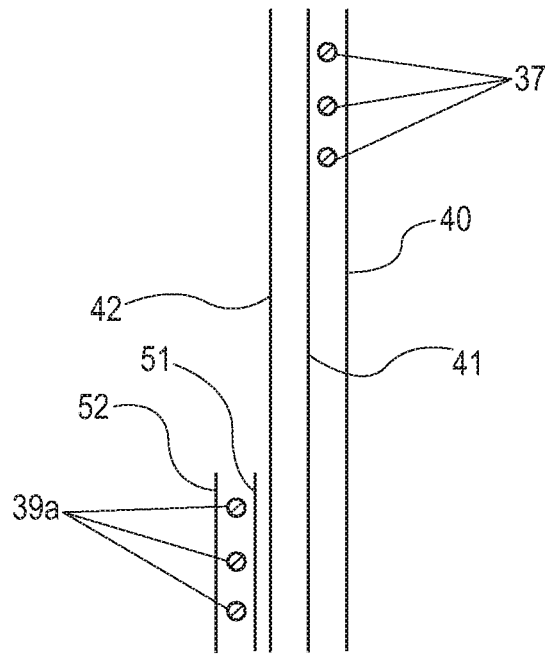
Figure 4G:
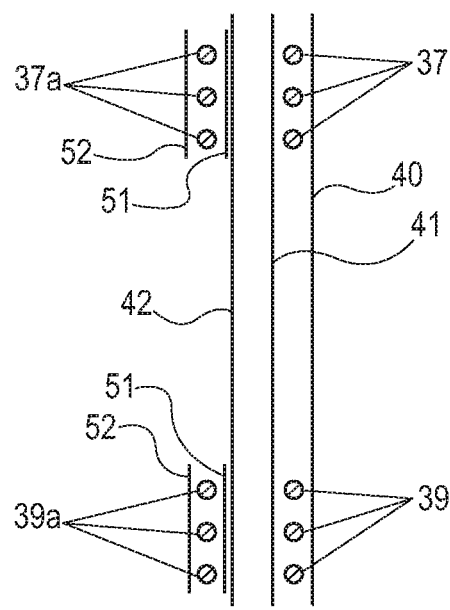
Figure 4H:
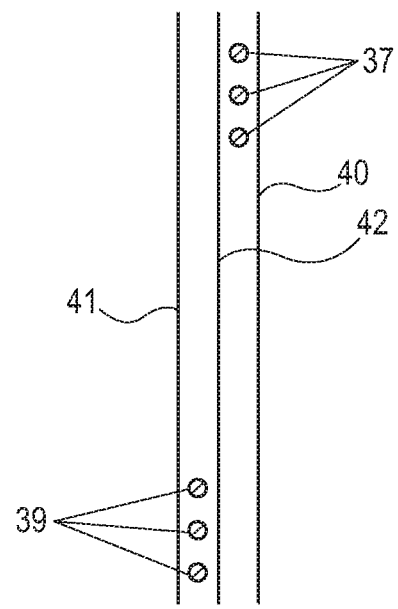
Figure 4I:
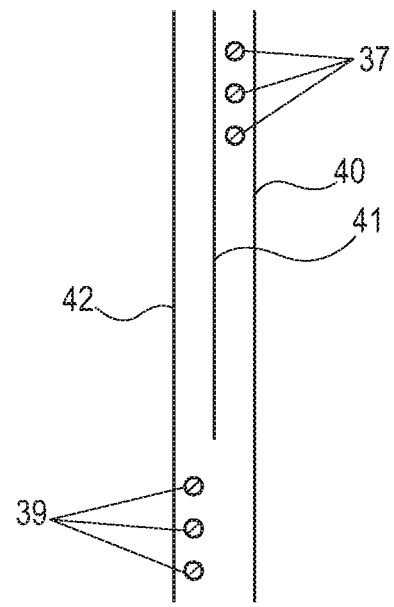
Figure 4J:
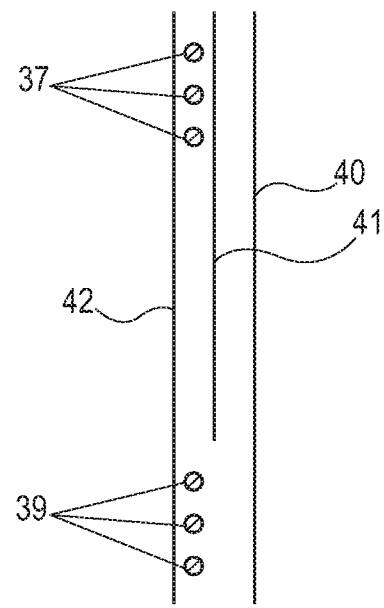
Figure 4K:
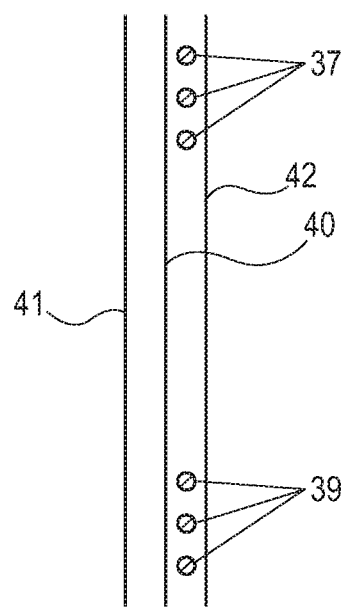

In still other examples, elastic members along the waist or leg band areas may be added about the waist opening or leg openings outside the outermost layer. Referring to FIGS. 4F and 4G, added elastic members 37a, 39a may be substituted for elastic members 37, 39, or my be supplemental to them. Added leg elastic members 39a and waist elastic members 37a may be first incorporated into elasticized band structures having inner and outer band layers 51, 52 as suggested in FIGS. 4F and 4G. The inner and outer band layers 51, 52 may be formed of respective nonwoven web materials, film materials or a combination thereof. In one example, a single layer may be folded over on itself to enclose and sandwich added elastic members 37a and/or 39a there between. In one embodiment the leg elastic members may be applied between two carrier layers in a linear fashion to create an elastic leg band laminate, and the elastic leg band laminate may subsequently be applied to the outermost layer or to a portion of the belt structure along a curvilinear path. Placing elastic laminates of outer band layers 51 and 52 with elastic members there between at the outer surfaces of the pant may provide a visual signal of stretchability and fit and a neat banded appearance, while moving the elastic members and resulting shirrs to the outer portions of the structure and away from the wearer's skin.

One or more of elastic members 36, 37, 38 and 39 may be varied from one or more of the others in various ways to impart differing stretch and force characteristics. For example, it may be desired that curvilinear leg elastic members exert greater or less tension about the leg openings than exists about the waist opening during wear, for fit snugness about these openings that differ according to specific design circumstances. One or more of the elastic members 36, 37, 38 and 39 may be selected and/or configured so as to differ from one or more of the others in a respect selected from number of elastic strands or bands, cross-sectional size of elastic strands or bands, cross-sectional shape of elastic strands or bands, chemical composition of material from which elastic strands or bands are formed, amount of pre-strain imparted to the elastic strands or bands during manufacture of the pant, spacing of the strands and combinations thereof.

In addition to the waist elastic members 36, 37 and curvilinear leg elastic members 38, 39, additional elastic members (not shown) may be included longitudinally there between, to impart additional stretch, contraction and load/force bearing capability to the belt structure, in the same manner as such capability is imparted by the waist and leg elastic members. The additional elastic members may be disposed between the same pairs of layers as any of elastic members 36, 37, 38 and 39, or may be disposed between differing pairs of layers, and may be disposed in alternating locations between differing pairs of layers as described above.

Some examples described above, as well as other examples not expressly described, may also be advantageous because they may lend themselves to relatively efficient manufacture.

Figure 5A:
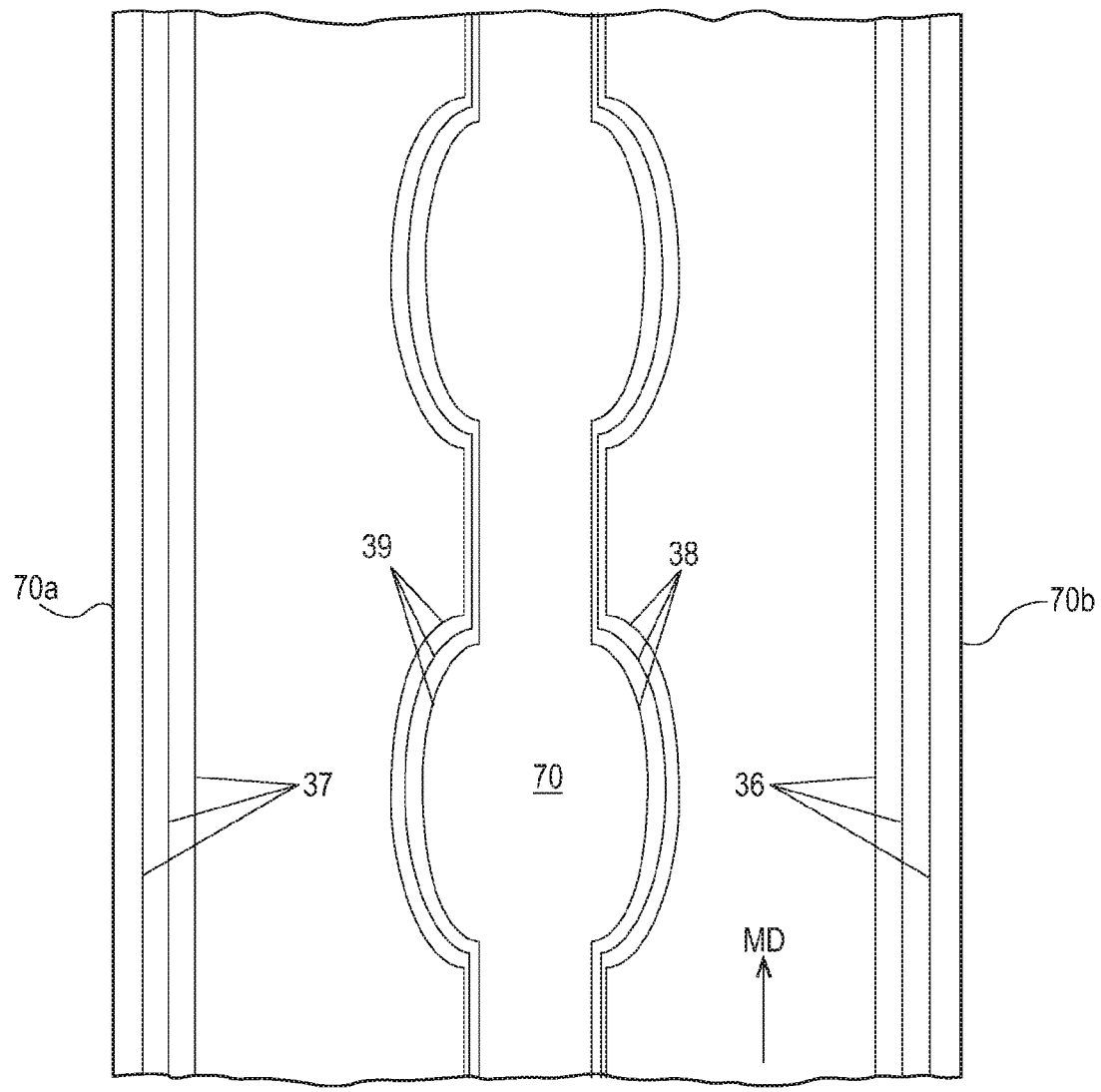
FIG. 5A is a plan view of a portion of a nonwoven web with applied elastic members.
Figure 5B:
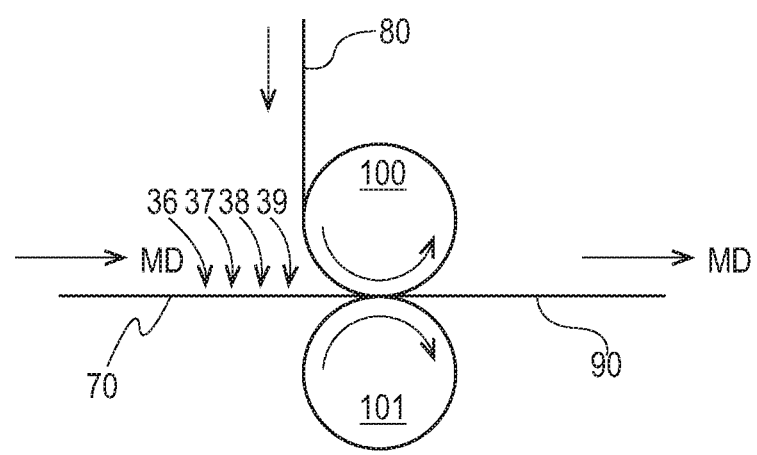
FIG. 5B is a simplified schematic view of equipment and components for manufacturing a laminate, shown along a cross-direction view.
Figure 7:
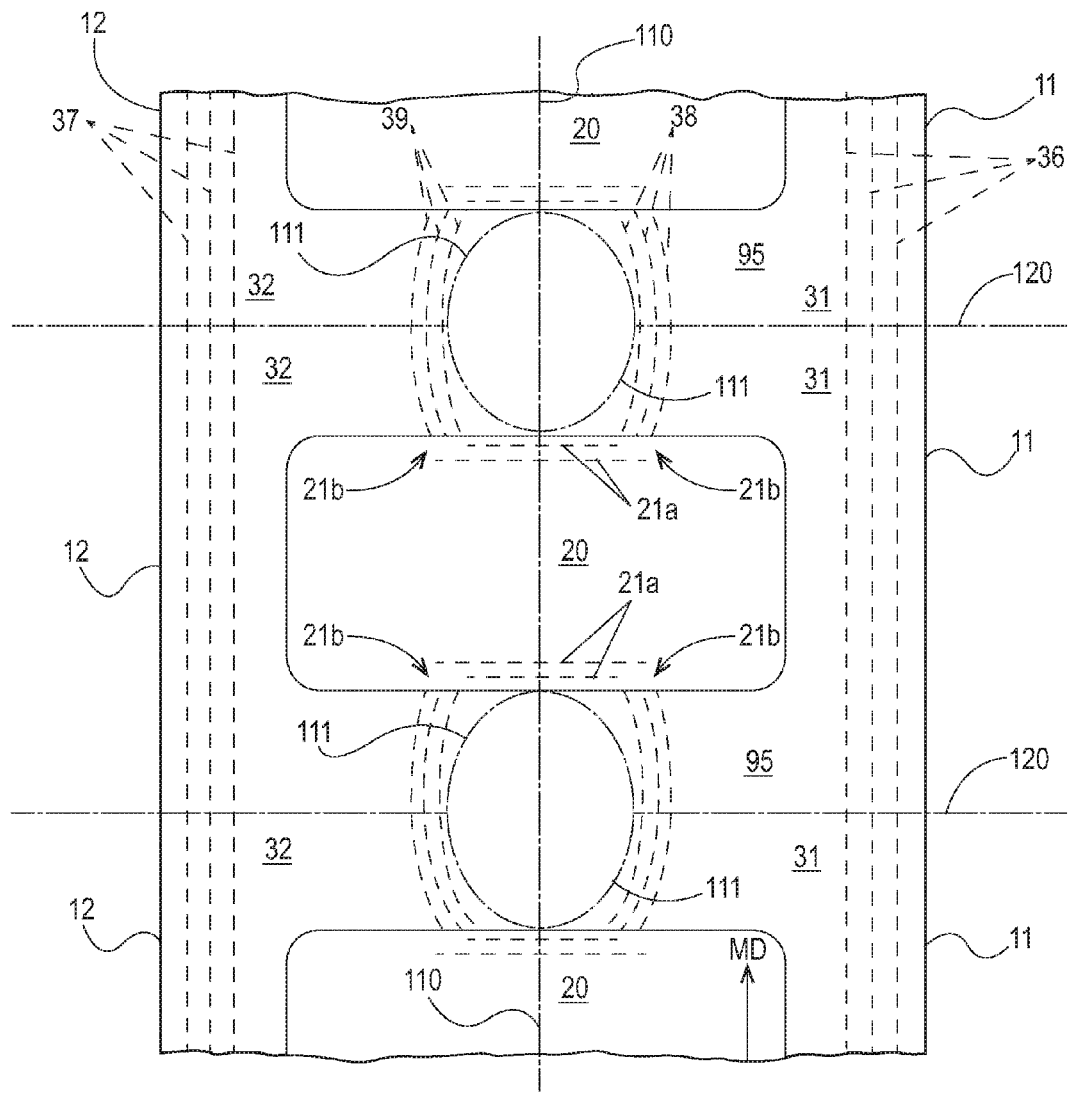
FIG. 7 is a plan view of a multilayer web and applied chassis structures illustrating a method for manufacturing pant structures.

Referring to FIGS. 5A and 5B, a first nonwoven web 70, to be used to form one of first belt layer 40 or second belt layer 41 for both front portion 31 and rear portion 32 (see FIG. 2), may be conveyed in a machine direction MD. As first nonwoven web 70 travels in the machine direction, one or more leg elastic members 38, 39 may be applied to the first nonwoven web 70 along one or more curvilinear paths. (Alternatively, some of the elastic members may be applied at a later step, as described below.) The respective curvilinear paths for elastic members 38, 39 may mirror each other about a machine direction axis along the web, or they may differ in some respects, to provide leg band profiles that vary from front to rear of the finished product. Referring to FIG. 7, the curvilinear paths for the elastic members 38, 39 may be arranged such that, when they are severed as described below, the severed ends are proximate to, and even meet, or align with, complement, and/or effectively form extensions of, leg cuff elastic members 21a present on leg cuff components of central chassis 20. This provides for the appearance and/or function of an elasticized leg band that completely encircles the wearer's leg. The leg elastic members may be applied along the curvilinear paths via methods and equipment described in, for example, U.S. Pat. Nos. 8,062,454 and 8,075,722 or U.S. application Ser. Nos. 12/362,981; 12/363,002; 12/363,023; and 12/363,048.

Simultaneously with, or before or after this step, one or more waist elastic members 36, 37 may be applied to the first nonwoven web 70 along substantially straight paths, and may be applied along the outer edges 70a, 70b of the web and may be spaced at equal or varying intervals there from, but so as to be disposed approximately along a lateral direction in the finished pant. In another example, the leg elastic members 38, 39, or fewer than all of them, may be applied to a second nonwoven web layer 80 and/or an outer surface of a first elasticized multilayer web 90, following lamination in rollers 100, 101 as depicted in FIG. 5B.

As they are applied to a web, the elastic members may be pre-strained by a controlled amount in the direction of their greater lengths, such that upon completion of manufacture and subsequent relaxation, shirrs of gathered nonwoven material are created that will accommodate elastic stretch when the pant is donned and worn. The elastic members may be adhered to web 70 along their paths of application by an adhesive applied to the web or to the elastic members or both, prior to application. Referring to FIG. 5B, following application of the waist elastic members and leg elastic members to web 70, first nonwoven web 70 and a second nonwoven web 80 (to form another of the component layers of a belt structure) may be passed through the nip between a first pair of laminating rollers 100, 101. If adhesive is applied to the surface at least one of the webs 70, 80 facing the other, passage through the laminating rollers will adhere the webs together and affix the elastic members in place between webs 70, 80 along their paths of application, and form a first elasticized multilayer web 90. In one example, the nonwoven web 80 may be a single continuous web extending across the cross direction to cover the entirety of web 70, or web 80 may be 2 separate webs spaced apart in the cross direction, to cover only the front and rear portions (i.e., relative FIG. 5A, the left and right portions) of web 70. Alternatively or in addition, one or both of rollers 100, 101 may have thereon a pattern of discrete bonding protrusions and one or both of rollers 100, 101 may have heating energy supplied thereto, such that a corresponding pattern of discrete bonds that affix webs 70, 80 together is impressed at the nip through heat, pressure or a combination thereof. It may be preferred, however, to use adhesive to form the laminate rather than heat/pressure bonding, since the latter method may damage the elastic members, and the former may be deemed more reliable to affix and hold the elastic members in place and prevent displacement of the elastic members relative to web 90, resulting from their tendency to contract following pre-strain. In another alternative, however, adhesive may be used to adhere the elastic members along their paths of application, and heat/pressure bonds may be used to affix the webs 70, 80 together in areas not occupied by the applied elastic members, the pattern of discrete bonding protrusions on one or both of rollers 100, 101 being arranged accordingly. In another alternative, the web 90 may be subjected to mechanical bonding following formation of the laminate.

The above-described steps provide for the securement and bonding of pre-strained elastic members, e.g., elastic members 38, 39, between two layers of nonwoven web, in a manner that reduces the likelihood that that they will substantially snap back and curl at their severed ends, when portions of the web including the elastic members 38, 39 are severed away as described below and illustrated in FIGS. 6A-6D. This provides for a neater appearance in the finished product about, e.g., leg openings, when such elastic members are severed proximate the leg openings.

Following its formation, in one alternative, first elasticized multilayer web 90 may be passed through incremental stretching and/or ring-rolling equipment to impart, promote formation of, or affect the appearance of an orderly pattern of shirrs in the layers, as described in, for example, U.S. Pat. Nos. 5,167,897; 5,156,793; and 5,143,679; or U.S. application Ser. Nos. 10/288,095; 10/288,126; 10/429,433; 11/410,170; 11/811,130; 11/899,656; 11/899,810; 11/899/811; 11/899,812; 12/204,844; 12/204,849; 12/204,854; 12/204,858; or 12/204,864 and the co-pending U.S. applications filed on the same day hereof in the names of Zink et al., U.S. App. Ser. Nos. 13/893,405, 13/893,634, and 13/893,735.

Referring to FIGS. 6A-6E, first elasticized multilayer web 90 may then be passed through cutting equipment that severs away middle section 97 from web 90 along cut paths 96, and middle section 97 may then be removed. This severs leg elastic members 38, 39 at repeated intervals as suggested in FIGS. 6A-6D, and leaves behind front and rear waist sections 98, 99 of first elasticized multilayer web 90. It may be appreciated from FIGS. 6B and 6D that cut paths 96 may also be nonlinear, and that a cutting die may be configured to cut along a cutting path that shifts in the cross direction, and/or is approximately parallel the path(s) of leg elastic members 38, 39. Also as suggested in FIGS. 6B and 6D, the cutting die may be configured to sever the leg elastic members and the associated web layer(s) in the cross direction so as to effect a longitudinally-oriented cut and arrangement of the severed ends of the leg elastic members in the finished pant, as suggested in FIGS. 1 and 2. Thus, in one example, it may be desired to cut elastic members 38, 39 along cross direction lines as suggested by cut paths 96 in FIG. 6B, rather than along machine direction lines as suggested by cut paths 96 in FIG. 6A. This enables the severed ends of elastic members 38, 39 to be neatly arranged longitudinally, i.e., at similar lateral locations, along the longitudinal edges 21 of the central chassis 20 (e.g., see FIGS. 1 and 2).

Following the severing of the leg elastic members, in one alternative, one or more waist elastic members may be applied to the front and rear waist sections 98, 99, in the event it is desired to supplement waist elastic members already added and disposed between the same pair of layers as the leg elastic members, or, in another alternative, in the event it is desired that waist elastic members be disposed between a differing pair of layers than leg elastic members 38, 39.

Figure 6A:
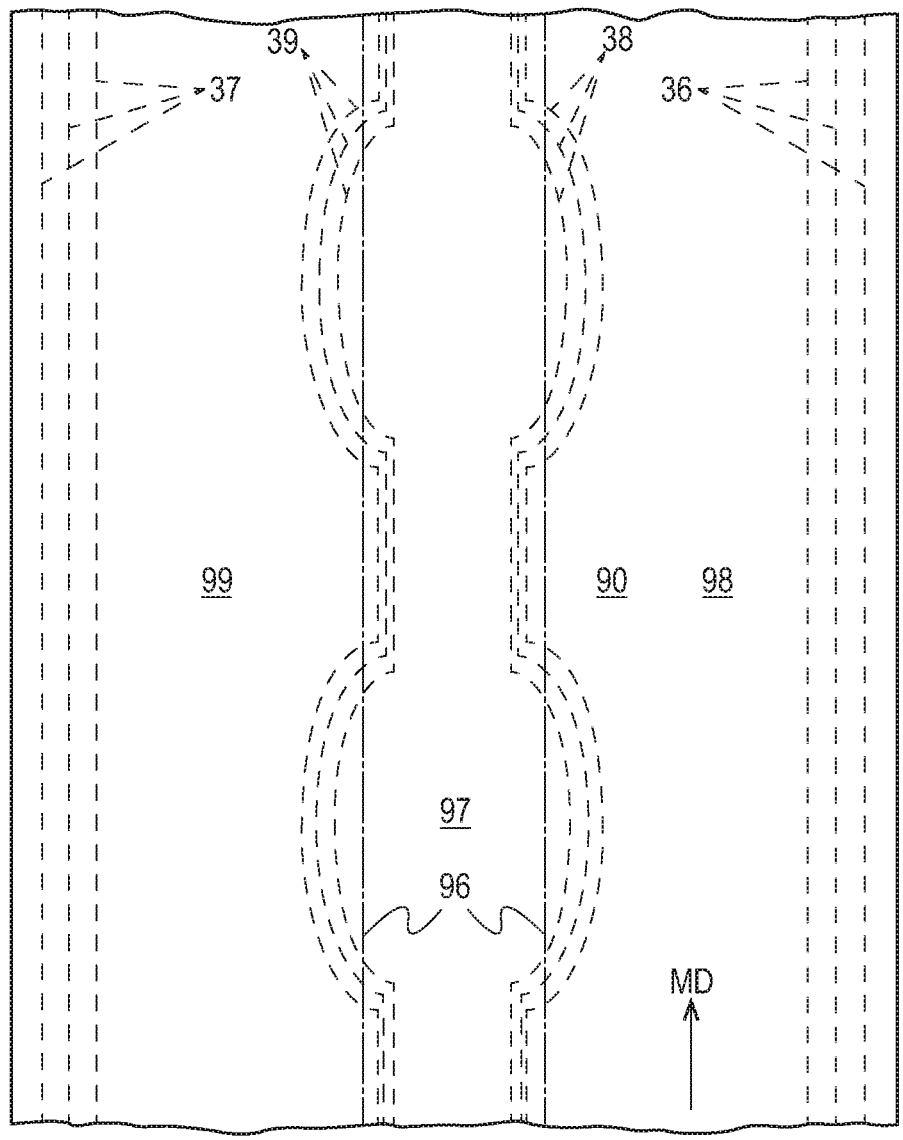
FIG. 6A is a plan view of a portion of a multilayer web shown with cut lines.
Figure 6B:
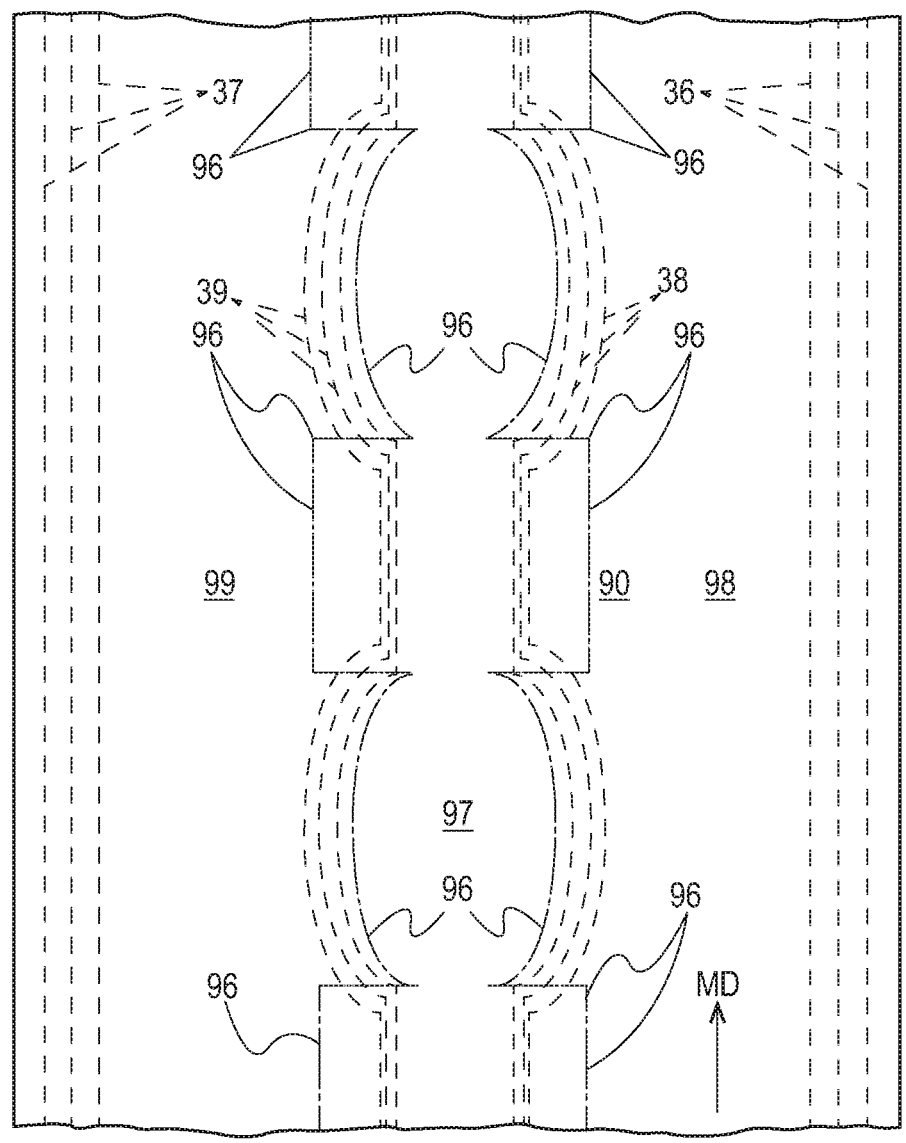
FIG. 6B is a plan view of a portion of a multilayer web shown with cut lines in an alternative configuration.
Figure 6C:
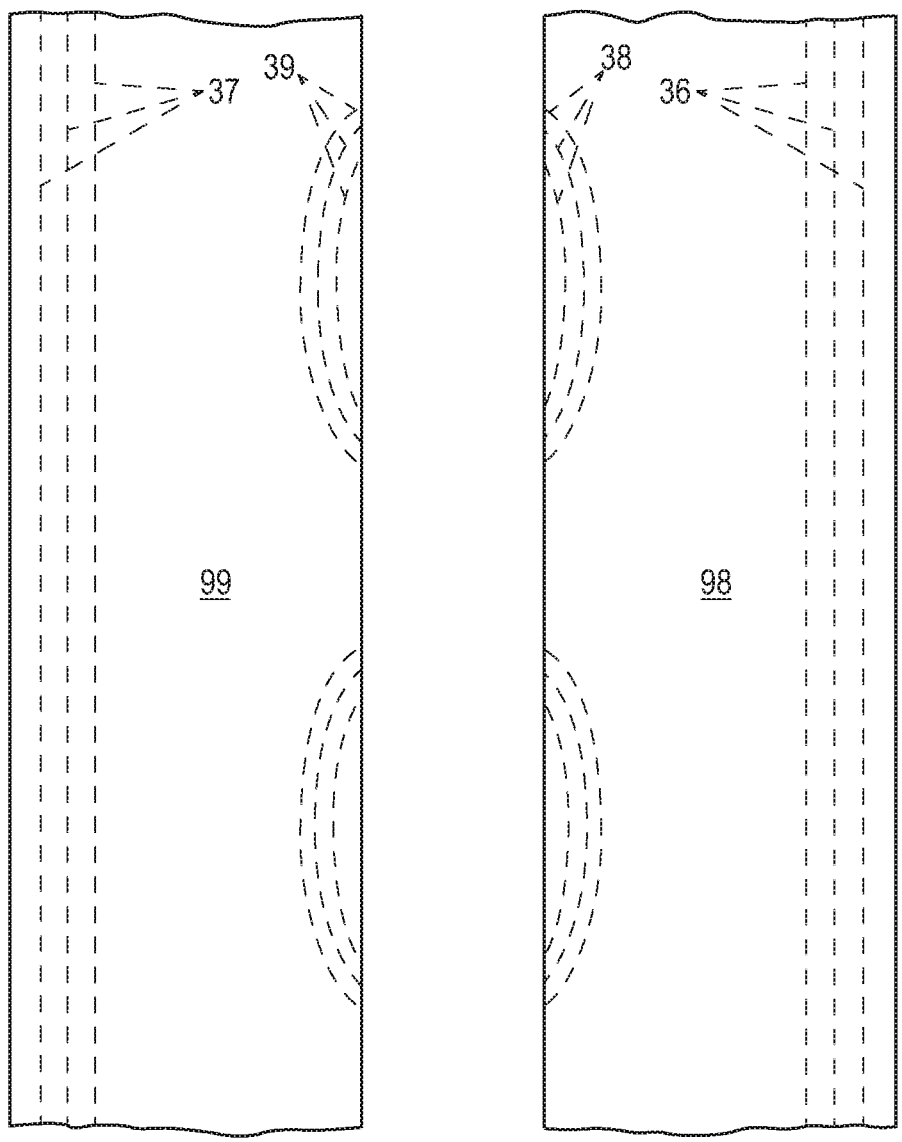
FIG. 6C is a plan view of portions of the multilayer web as shown in FIG. 6A, with a middle section severed away.
Figure 6D:
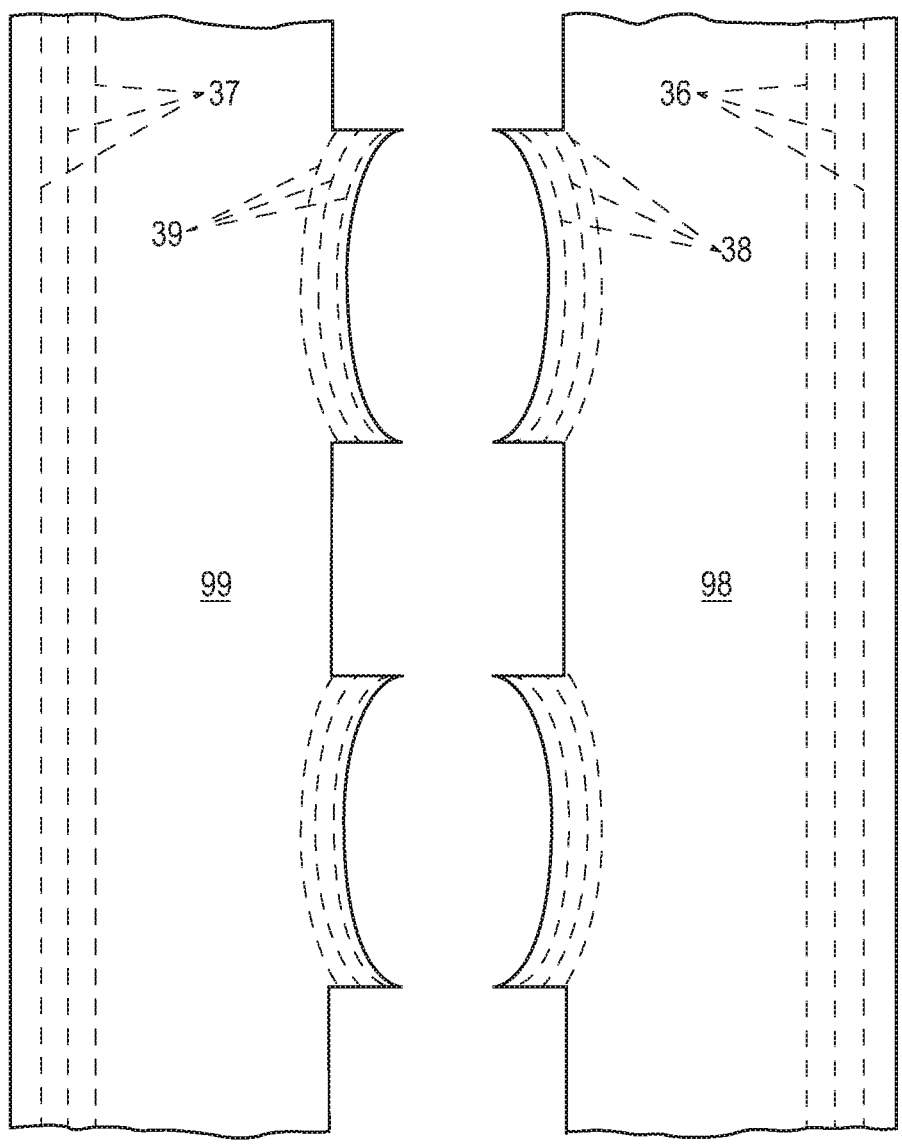
FIG. 6D is a plan view of portions of the multilayer web as shown in FIG. 6B, with a middle section severed away.
Figure 6E:
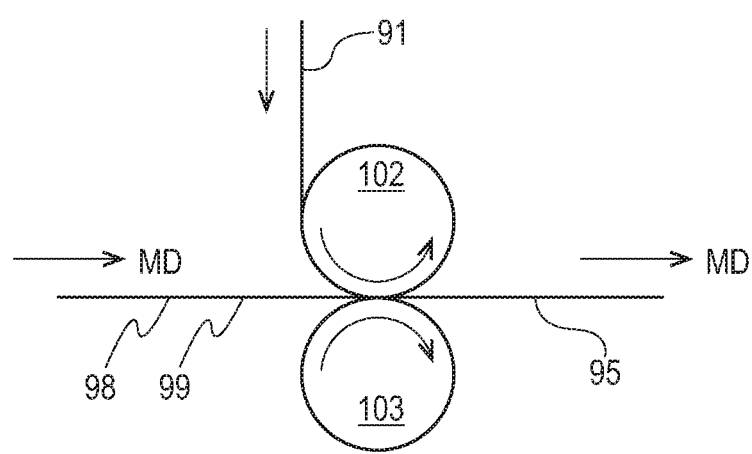
FIG. 6E is a simplified schematic view of equipment and components for manufacturing a laminate, shown along a cross-direction view.

Referring to FIG. 6E, front and rear waist sections 98, 99 together with a third layer web 91 (which also may be a nonwoven web) may then be passed through the nip between a second pair of laminating rollers 102, 103 to form a second elasticized multilayer web 95 that is a precursor to a belt structure. Prior to passing front and rear waist sections 98, 99, and web 91 through the nip between rollers 102, 103, one or both of the front and rear waist sections 98, 99 may be shifted in the cross direction to increase or decrease the spacing between the front and rear belt sections. Additionally, one or both of the front and rear waist sections may be allowed to partially (but not entirely) relax and contract along the machine direction through contraction of the pre-strained elastic members. This will allow third layer web 91 to be applied to the laminate in a manner that results in shins in web 91 about the elastic members that are fewer in number, and/or lower in height/depth, and/or spaced differently, compared with those resulting in the first and second nonwoven webs in the finished product, and thereby, provide a differing appearance and/or feel to the outer layer web component of the belt structure. Third layer web 91 may be affixed to front and rear waist sections 98, 99 by adhesive applied to one or more of the acing surfaces thereof in a continuous web-like application, or a continuous or discontinuous pattern; as noted above, the pattern may be configured to affect the features of shirrs that appear in the third layer. Alternatively or in addition, one or both of rollers 102, 103 may have thereon a pattern of discrete bonding protrusions and one or both of rollers 102, 103 may have heating energy supplied thereto, such that a corresponding pattern of discrete bonds that affix webs 90, 91 together is impressed at the nip through heat, pressure or a combination thereof. The pattern may be arranged so as to avoid the areas occupied by the elastic members so as not to damage them, and to provide an appearance that does not have a distinct pattern of shirrs.

There are several advantages provided by including a third layer (in addition to elastic members) in the belt structure as described herein. First, as described above, including three layers allows for formation of a differing pattern of shirrs, exposed on either the inside or outside of the belt structure, than the pattern formed in the first two layers. Second, inclusion of a third layer provides options concerning the locations of elastic members in differing areas (e.g., waistband area and legband area) between differing pairs of layers. See, e.g., FIGS. 4A-4C, 4D, 4E, and 4H-4J. This allows the manufacturer to manipulate the mechanical properties, comfort and appearance of the belt structure.

Following its formation, in one alternative, second elasticized multilayer web 95 may be passed through incremental stretching and/or ring-rolling equipment to impart or promote formation of an orderly pattern of shirrs in the layers, as described in, for example, U.S. Pat. Nos. 5,167,897; 5,156, 793; and 5,143,679; or U.S. application. Ser. Nos. 10/288, 095; 10/288,126; 10/429,433; 11/410,170; 11/811,130; 11/899,656; 11/899,810; 11/899,811; 11/899,812; 12/204, 844; 12/204,849; 12/204,854; 12/204,858; or 12/204,864 and the co-pending U.S. applications filed on the same day hereof in the names of Zink et al., U.S. App. Ser. Nos. 13/893,405, 13/893,634, and 13/893,735.

Following that step, referring to FIG. 7, central chassis 20 structures may be applied to either surface of second elasticized multilayer web 95 and affixed thereto by any suitable method including thermal bonding, adhesive bonding, mechanical fastening or a combination thereof. Where central chassis 20 includes elasticized leg cuff structures, for example, such as described in U.S. provisional patent application No. 61/480,663, with leg cuff elastic members 21*a*, these may be directly affixed to the belt structure at cuff bonding locations 21*b* proximate the severed ends of leg elastic members 38, 39; this may provide for effective creation of an elasticized cuff/banding structure that substantially or entirely encircles the wearer's leg.

Lastly, individual pant precursor structures such as shown in FIG. 2 may be severed and separated from the web along separation lines 120. Simultaneously with or prior this severing step, leg opening cutouts 111 may be made in the outer layer web 91 component of web 95. A single rolling cutting die may be made and paired with an anvil roller to form a cutting nip that effects cutting along separation lines 98 and leg cutouts 111 in a single operation. (As noted above, in another alternative, leg opening cutouts may be made simultaneously with the cutting step described above in which middle section 97 is cut away, along cut lines 96, as suggested in FIGS. 6B and 6D.) The final cutting step severing the web along separation lines 120 sever away individual pant precursor structures, such as shown in FIG. 2, for example.

In another alternative, however, the entire second elasticized web 95 combined with applied central chassis 20 structures, may be passed through a folding device (not shown) prior to severing away individual pant structures. The folding device may be configured to fold the entire combined web 95 and chassis 20 structure along a fold line 110 extending in the machine direction, central chassis 20 to the inside of the fold, thereby bringing front portions 31 and rear portions 32 together prior to severing away pant structures. Thereafter, the combined, folded web 95 and central chassis 20 may be passed through seaming and cutting equipment that forms seams along both sides of separation lines 120, joining front portions 31 and rear portions 32 at side seams 33*r*, 33*l* (see FIG. 1), and severs away individual pants 10 from the web 95. It may be desirable that this final seaming and cutting operation be performed simultaneously, wherein the seaming and cutting equipment includes a seaming and cutting die configured to simultaneously compress the web material along both sides of separation lines 120, and cut the material along separation lines 120. Heating energy may be supplied to the seaming and cutting equipment such that the compression effects thermal bonding of the web materials to form the seams 33*r*, 33*l*.

An advantage that may be provided by the foregoing manufacturing steps is that they provide for the severing of the leg elastic members 38, 39 such that they terminate neatly at locations proximate the longitudinal edges 21 of central chassis 20 (see FIG. 2), while their severed ends are held in place and prevented from retracting by being held in place within the laminate structure. This eliminates an unsightly continuation of these elastic members across the front and rear of the chassis, as is present in some currently marketed pant designs. Other currently marketed pant designs have severed leg elastics that terminate proximate longitudinal edges of a chassis, but exhibit substantial "snap back," wherein the severed ends of elastic members have retracted and/or curled about within the structure, providing an unfinished, unsightly appearance. The steps described above, in which the elastic members are adhered or otherwise secured between layers of a laminate structure prior to any severing, may help avoid this effect.

Hysteresis Test

Obtain samples of subject material sufficient to provide for a gauge length of at least 15 mm along the direction of stretch in the Test, and should be of a constant width (perpendicular to the direction of stretch in the Test) of at least 5 mm.

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate grips and load cell. The grips must have flat surfaces and must be wide enough to grasp the sample along its full width. Also, the grips should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length) at 15 mm.

4. Place the sample in the flat surfaces of the grips such that the uniform width lies along a direction perpendicular to the gauge length direction. Secure the sample in the upper grips, let the sample hang slack, then close the lower grips. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100.

5(a) First cycle loading: Pull the sample to the specified strain (herein, 100%) at a constant cross head speed of 100 mm/min. Report the stretched sample length between the grips as $l_{max}$.

5(b) First cycle unloading: Hold the sample at the specified strain for 30 seconds and then return the crosshead to its starting position (0% strain or initial sample length, $l_{ini}$) at a constant cross head speed of 100 mm/min. Hold the sample in the unstrained state for 1 minute.

5(c) Second cycle loading: Pull the sample to the specified strain at a constant cross head speed of 100 mm/min.

5(d) Second cycle unload: Next, return the crosshead to its starting position (i.e. 0% strain at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

i. Length of sample between the grips at a slack preload of 0.02 N/cm ($l_{ini}$) to the nearest 0.001 mm.

ii. Length of sample between the grips on first cycle at the specified strain ($l_{max}$) to the nearest 0.001 mm.

iii. Length of sample between the grips at a second cycle load force of 0.02 N/cm ($l_{ext}$) to the nearest 0.001 mm.

iv. % set, which is defined as $(l_{ext}-l_{ini})/(l_{max}-l_{ini})*100\%$ to the nearest 0.01%.

The testing is repeated for six separate samples and the average and standard deviation reported.

The Hysteresis Test can be suitably modified depending on the expected attributes and/or properties of the particular material sample to be measured. For example, the Test can be suitably modified where a sample of the length and width specified above are not available from the subject pant.

All patents and patent applications (including any patents which issue thereon) referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended that the scope of the invention is limited only by the appended claims and equivalents thereof.

What is claimed is:

1. A disposable absorbent pant having a front waist region, a rear waist region, and a crotch region, and comprising:
    a central chassis occupying the crotch region and comprising left and right longitudinal edges; a liquid permeable topsheet; a backsheet, and an absorbent core disposed between the topsheet and the backsheet;
    a belt structure disposed about the central chassis, the belt structure comprising an elasticized multilayer web overlaying a garment-facing surface of the backsheet in the front and rear waist regions, the belt structure extending laterally outward from the chassis and from each of the left and right longitudinal edges in each of the front and rear waist regions, the belt structure having a front portion having a front waist edge, front left and right leg opening edges, and front left and right side edges, and the belt structure having a rear portion having a rear waist edge, rear left and right leg opening edges, and rear left and right side edges, the respective front and rear left side edges and the respective front and rear right side edges being joined at side seams, the belt structure forming a waist opening and left and right leg openings, wherein each of the front and rear portions of the belt structure further comprises:
    an inner layer formed of an inner nonwoven web;
    an outer layer formed of an outer nonwoven web;
    an intermediate layer formed of an intermediate nonwoven web, and
    disposed between the inner layer and the outer layer;
    a waist elastic member disposed between the inner layer and the outer layer, extending continuously in a lateral direction across the portion, and having terminal ends proximate the side edges; and
    left and right leg elastic members each disposed between the inner layer and the outer layer, each extending continuously along a curvilinear path along and proximate at least a portion of the respective left or right leg opening edge and each having a terminal end proximate the respective left or right longitudinal edge of the chassis, and proximate the respective left or right side edge; and
    a plurality of shins in at least one of the inner layer, intermediate layer or outer layer, lying about and oriented transversely to paths occupied by the waist and leg elastic members;
    wherein at least one of the inner and outer layers is a wrapping layer that lies over a garment-facing surface of the central chassis, through the crotch region,
    wherein an added elastic member is disposed on a garment-facing surface of the outer layer, and wherein the added elastic member is disposed proximate one of the leg edges so as to be disposed nearer one of the leg edges than one of the waist edges.

2. The pant of claim 1 wherein the waist elastic member of each of the front and rear portions of the belt structure is disposed along and proximate the respective front or rear waist edge.

3. The pant of claim 1 wherein the waist elastic member and the left and right leg elastic members in each of the front and rear portions of the belt structure are disposed between the inner layer and the intermediate layer thereof.

4. The pant of claim 1 wherein one of the waist elastic member and left and right leg elastic members in each of the front and rear portions of the belt structure is disposed between the inner layer and the intermediate layer thereof, and another of the waist elastic member and left and right leg elastic members in each of the front and rear portions of the belt structure is disposed between the intermediate layer and the outer layer thereof.

5. The pant of claim 1 wherein the waist elastic member and the left and right leg elastic members in each of the front and rear portions of the belt structure are disposed between the intermediate layer and the outer layer thereof.

6. The pant of claim 1 wherein each of the front and rear portions of the belt structure further comprises a third elastic member disposed between the inner layer and the outer layer and disposed between the waist elastic member and the leg elastic members.

7. The pant of claim 1 wherein the added elastic member is disposed in an elasticized band structure between inner and outer band layers.

8. The pant of claim 7 wherein the added elastic member comprises a plurality of elastic strands disposed in the elasticized band structure between the inner and outer band layers.

9. The pant of claim 1 wherein the waist elastic member and the leg elastic members in either or both the front portion and the rear portion of the belt structure differ from each other in a respect selected from the group consisting of number of elastic strands or bands, cross-sectional size of elastic strands or bands, cross-sectional shape of elastic strands or bands, chemical composition of material from which elastic strands or bands are formed, amount of pre-strain imparted during manufacture, and combinations thereof.

10. A disposable absorbent pant having a front waist region, a rear waist region, and a crotch region, and comprising:
  a central chassis occupying the crotch region and comprising left and right longitudinal edges; a liquid permeable topsheet; a liquid impermeable backsheet, and an absorbent core disposed between the topsheet and the backsheet;
  a belt structure disposed about the central chassis, the belt structure comprising an elasticized multilayer web overlaying a garment-facing surface of the backsheet in the front and rear waist regions, the belt structure extending laterally outward from the chassis and from each of the left and right longitudinal edges in each of the front and rear waist regions, the belt structure having a front portion having a front waist edge, front left and right leg opening edges, and front left and right side edges, and the belt structure having a rear portion having a rear waist edge, rear left and right leg opening edges, and rear left and right side edges, the respective front and rear left side edges and the respective front and rear right side edges being joined at side seams, the belt structure forming a waist opening and left and right leg openings, wherein each of the front and rear portions of the belt structure further comprises:
  an inner layer formed of an inner nonwoven web;
  an outer layer formed of an outer nonwoven web;
  an intermediate layer formed of an intermediate nonwoven web, and disposed between the inner layer and the outer layer;
  a waist elastic member disposed between the inner layer and the outer layer, extending continuously in a lateral direction across the portion, and having terminal ends proximate the side edges; and
  left and right leg elastic members each disposed between the inner layer and the outer layer, each extending continuously along a curvilinear path along and proximate at least a portion of the respective left or right leg opening edge and each having a terminal end proximate the respective left or right longitudinal edge of the chassis, and proximate the respective left or right side edge; and
  a plurality of shins in at least one of the inner layer, intermediate layer or outer layer, lying about and oriented transversely to paths occupied by the waist and leg elastic members;
wherein at least one of the inner, intermediate and outer layers is a wrapping layer that lies over a garment-facing surface of the central chassis through the crotch region,
wherein an added elastic member is disposed on a garment-facing surface of the outer layer, and
wherein the added elastic member is disposed proximate one of the leg edges so as to be disposed nearer one of the leg edges than one of the waist edges.

* * * * *

UNITED STATES PATENT AND TRADEMARK OFFICE
CERTIFICATE OF CORRECTION

PATENT NO. : 9,289,332 B2  
APPLICATION NO. : 13/893604  
DATED : March 22, 2016  
INVENTOR(S) : Sarah Marie Wade et al.

Page 1 of 1

It is certified that error appears in the above-identified patent and that said Letters Patent is hereby corrected as shown below:

Claims

Column 14, line 50, claim 1, delete "shins" and replace with – shirrs –
  Column 16, line 33, claim 10, delete "shins" and replace with – shirrs –

Signed and Sealed this
Fourteenth Day of June, 2016

Michelle K. Lee
*Director of the United States Patent and Trademark Office*